US00PP20316P2

(12) United States Plant Patent
Klaveren

(10) Patent No.: US PP20,316 P2
(45) Date of Patent: Sep. 15, 2009

(54) ***HYDRANGEA* PLANT NAMED 'ZULU'**

(50) Latin Name: *Hydrangea macrophylla*
Varietal Denomination: Zulu

(76) Inventor: Arie D. Klaveren, Hoofdweg 149, De Kwakel, 1424 PE (NL)

( * ) Notice: Subject to any disclaimer, the term of this patent is extended or adjusted under 35 U.S.C. 154(b) by 0 days.

(21) Appl. No.: 12/283,649

(22) Filed: Sep. 15, 2008

(51) Int. Cl.
*A01H 5/00* (2006.01)

(52) U.S. Cl. ..... Plt./250
(58) Field of Classification Search ..... Plt./250
See application file for complete search history.

*Primary Examiner*—Kent L Bell
(74) *Attorney, Agent, or Firm*—Penny J. Aguirre

(57) ABSTRACT

A new cultivar of *Hydrangea macrophylla* named 'Zulu' that is characterized by its strong stems that are dark purple-brown to purple-black in color, its dwarf plant habit, its dark green foliage, and its mophead type inflorescences that form a flattened mound and are pink in color (bluer in color depending with alkaline pH and sufficient aluminum levels).

3 Drawing Sheets

Genus/species: *Hydrangea macrophylla.*
Varietal denomination: 'Zulu'.

BACKGROUND OF THE INVENTION

The present invention relates to a new and distinct cultivar of *Hydrangea macrophylla* and will be referred to hereafter by its cultivar name, 'Zulu'. 'Zulu' represents a new Bigleaf *Hydrangea,* a deciduous shrub grown for landscape use and for use as a potted plant.

'Zulu' arose from an open pollination in June 2003 in his nursery in De Kwakel, The Netherlands. 'Zulu' was selected as a single unique plant from amongst seedlings that were grown in a seedbed and derived from open pollination of *Hydrangea macrophylla* 'Blaumeise' (not patented). The male parent of 'Zulu' is unknown.

Asexual reproduction of the new cultivar was first accomplished by softwood stem cuttings in De Kwakel, The Netherlands in July of 2004 by the inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Zulu' as a unique cultivar of *Hydrangea macrophylla.*

1. 'Zulu' exhibits strong stems that are dark purple-brown to purple-black in color.
2. 'Zulu' has Hortensia type inflorescences that form a flattened mound and are pink in color with a light green eye, but typical of *Hydrangea macrophylla* will be bluer in color depending with alkaline pH and sufficient aluminum levels.
3. 'Zulu' exhibits a dwarf habit, reaching about 45 cm in height when one year in age from a rooted cutting.
4. 'Zulu' exhibits dark green foliage.

'Zulu' differs from 'Blaumeise', in that 'Blaumeise' has Lacecap type inflorescences, green stems, and reaches about 1.5 m in height when one year in age. The new cultivar of *Hydrangea* can be compared to *Hydrangea macrophylla*

'Zorro' (U.S. Plant Pat. No. 18,255), which is similar to 'Zulu' in height and in having dark purple-brown stems. 'Zorro' differs in having Lacecap type inflorescences. 'Zulu' can also be compared to *Hydrangea macrophylla* 'Nigra' (not patented), which is similar to 'Zulu' in having Hortensia type blooms and in having dark purple-brown stems. 'Nigra' differs from 'Zulu' in having a greater plant height, in having thinner stems, more globose-shaped inflorescences and in having light green foliage.

BRIEF DESCRIPTION OF THE DRAWINGS

The accompanying photographs were taken of a one year-old plant of 'Zulu' as grown outdoors in a 23 cm container in De Kwakel, The Netherlands.

The photograph in FIG. 1 provides a side-view of a plant of 'Zulu' in bloom.

Figure 1:
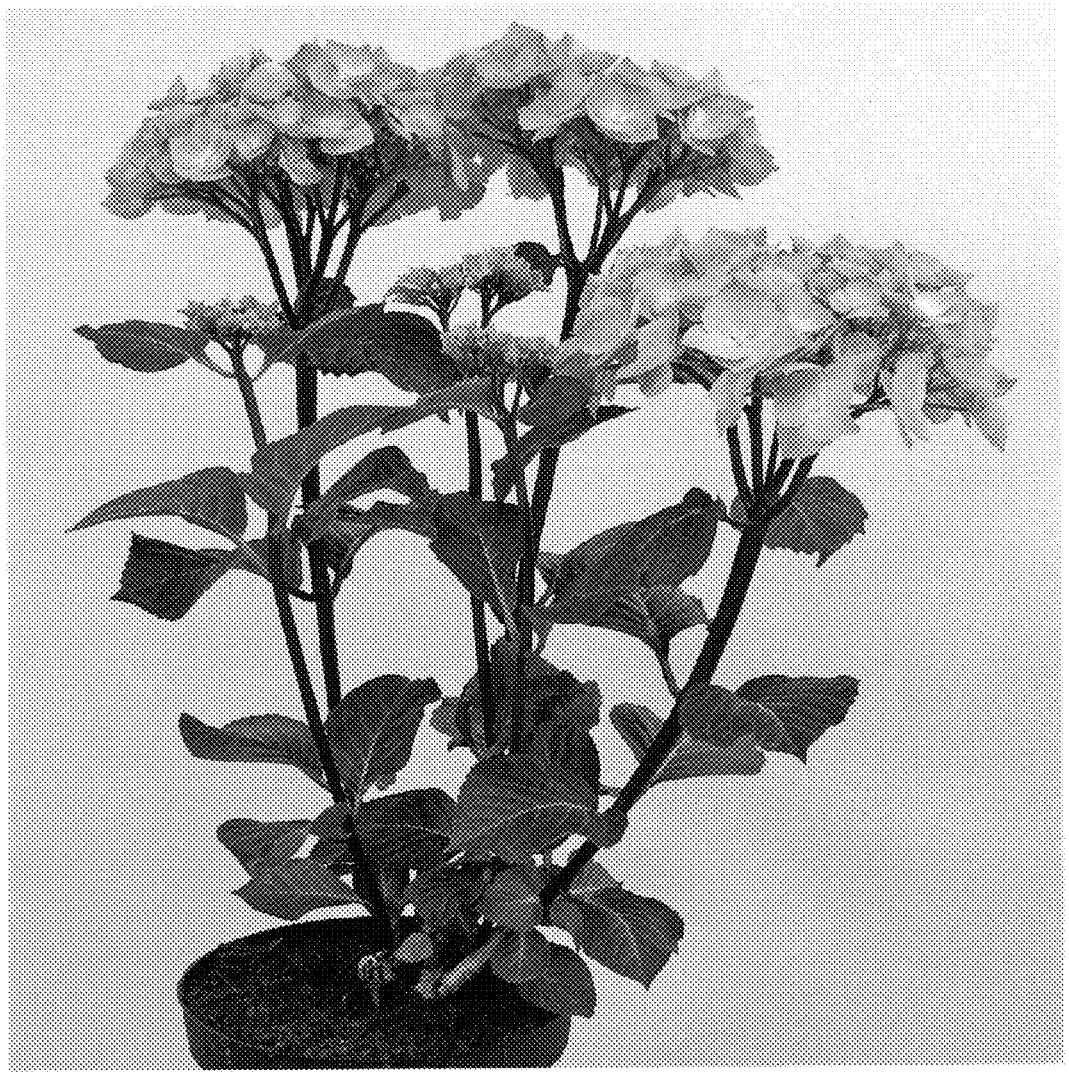
Figure 2:
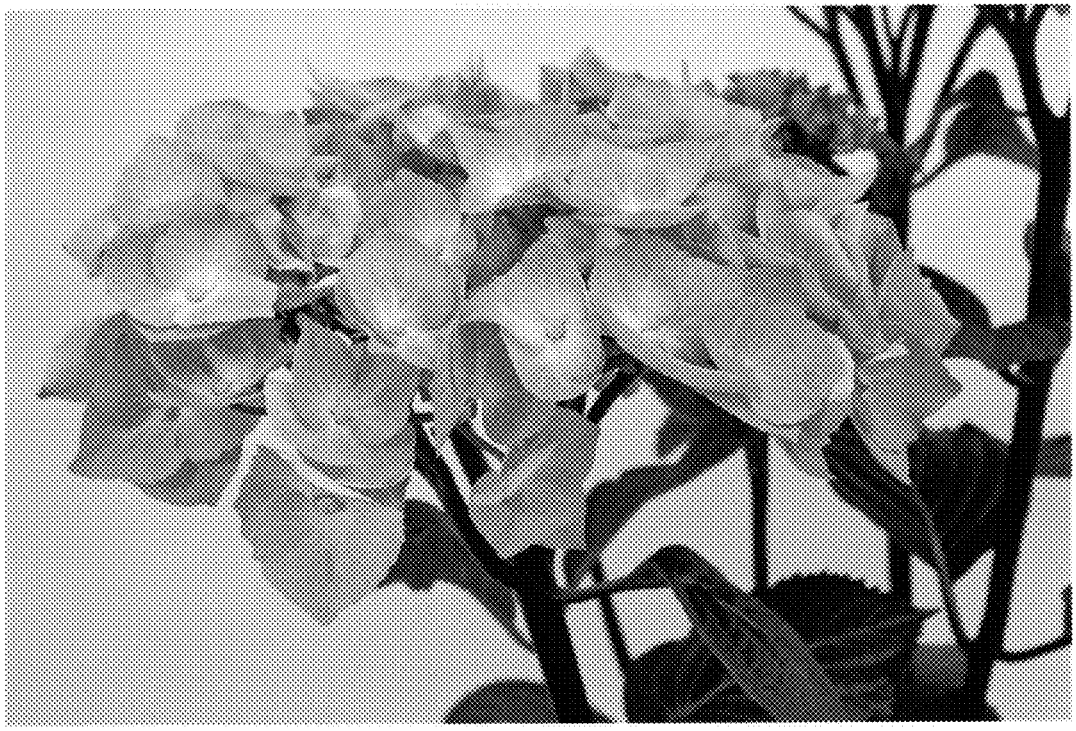

The photograph in FIG. 2 provides a close-up view of an inflorescence of 'Zulu'.

Figure 3:
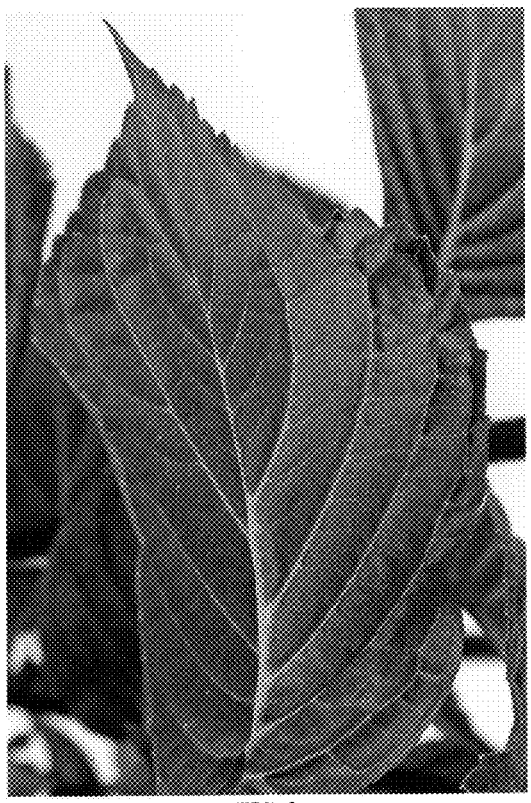
Figure 4:
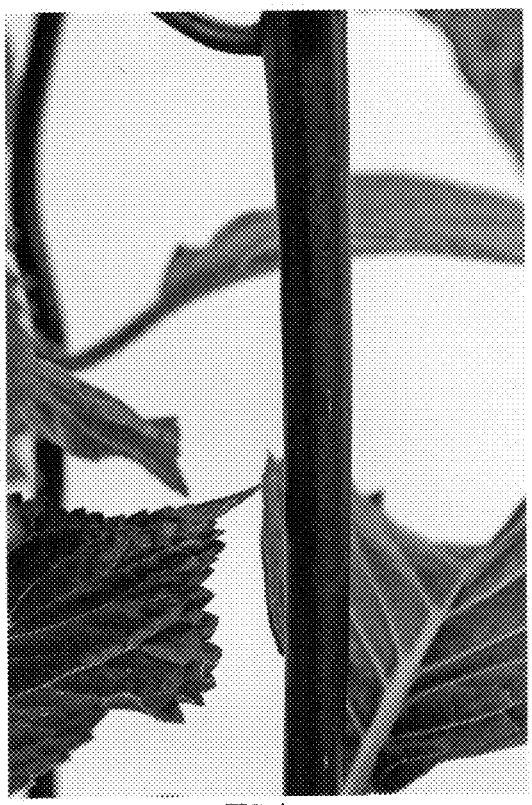

The photograph in FIG. 3 provides a close-up view of a leaf of 'Zulu' and the photograph in FIG. 4 provides a close-up view of a stem of 'Zulu'.

The colors in the photographs are as close as possible with the digital photography and printing techniques utilized and the color codes in the detailed botanical description most accurately describe the new *Hydrangea.*

BOTANICAL DESCRIPTION OF THE PLANT

The following is a detailed description of one year-old plants of the new cultivar as grown in 23 cm containers under ambient light, outdoors in De Kwakel, The Netherlands. Phenotypic differences may be observed with variations in environmental, climatic, and cultural conditions. The color determination is in accordance with the 2001 R.H.S. Colour Chart of The Royal Horticultural Society, London, England, except where general color terms of ordinary dictionary significance are used.

Botanical classification: 'Zulu' is a cultivar of *Hydrangea macrophylla.*

Commercial classification: Bigleaf *hydrangea.* Hortensia type.

General description:

*Blooming period*.—Spring blooming in The Netherlands.

*Plant habit*.—Broadly upright, deciduous shrub.

*Height and spread*.—Reaches about 45 cm in height and 30 cm width in one year.

*Cold hardiness*.—At least to U.S.D.A. Zone 5.

*Heat tolerance*.—Known to tolerate temperatures of at least 35° C.

*Diseases resistance*.—No susceptibility or resistance to diseases known to effect *H. macrophylla* has been observed.

*Root description*.—Fine.

Growth and propagation:

*Propagation*.—Softwood stem cuttings.

*Time required for root development*.—About 3 weeks to fully develop in a liner as grown under greenhouse conditions at an average temperature of 20° C.

*Time required to produce a salable crop*.—About 12 months from propagation to a flowering plant in a 15 cm or larger container.

*Growth rate and vigor*.—Moderate, growth rate is about 10 cm per month in spring.

Stem description:

*Stem shape*.—Round, solid.

*Stem strength*.—Very strong.

*Stem color*.—Young stems; a color between N186B to 186C, 200A and 202A, older bark; N199C.

*Stem size*.—Average of 33 cm (to base of inflorescence), average of 8 mm in width.

*Stem surface*.—Glabrous and glossy.

*Branching*.—An average of 6 lateral branches.

Foliage description:

*Leaf shape*.—Broadly oval.

*Leaf arrangement*.—Opposite.

*Leaf division*.—Simple.

*Leaf number*.—Average of 8 (4 pairs) per lateral branch.

*Leaf internode length*.—Average of 9.5 cm.

*Leaf base*.—Rounded to short attenuate.

*Leaf apex*.—Acuminate.

*Leaf margins*.—Serrated.

*Leaf venation*.—Pinnate, recessed on upper surface, color 144C to 144D on upper surface and 146D on lower surface.

*Leaf size*.—Average of 12.2 cm in length and 8.6 cm in width.

*Leaf attachment*.—Petiolate.

*Leaf surface*.—Glabrous and slightly glossy on upper and lower surface.

*Leaf color*.—Young foliage upper surface; 139A to 147A, young foliage lower surface; 146A, mature foliage upper surface; a color between 139A and 147A (closest to 147A), mature foliage lower surface; 137B to 137C.

*Petioles*.—Average of 2.1 cm in length and 5 mm in width, a color between N186C and 200A but slightly darker.

Inflorescence description:

*Inflorescence type*.—Terminal compound corymb, slightly flattened shape, fertile flowers are primarily hidden by sterile flowers.

*Lastingness of inflorescence*.—Persistent but color is retained for about 4 weeks.

*Inflorescence number*.—One per lateral or sublateral stem if pinched.

*Inflorescence size*.—Average of 14.5 cm in height and 22.2 cm in diameter.

*Flower number*.—Numerous, average of 175 sterile flowers and 100 fertile flowers per inflorescence.

*Flower fragrance*.—None.

*Time required to develop an inflorescence*.—Approximately 9 weeks after growth emerges when container grown.

*Flower aspect*.—Outward to upright.

*Flower size*.—Sterile flowers; An average of 5.7 cm in diameter and 1.6 cm in depth, fertile flowers; average of 1 cm in diameter and 7 mm in depth.

*Flower buds*.—Fertile flowers; an average of 6 mm in length and 5 mm in diameter prior to opening, broadly ovate in shape, color 157A tinged with 115A to 115B with base 143B to 143C, sterile flowers; an average of 3 cm in length and 6 mm in diameter, broadly ovate in shape, color 144A to 144B.

*Peduncles*.—Strong, an average of 8.5 cm in length and 4.5 mm in width, held at about a 30° angle from vertical, N186C to N186D in color, surface is glabrous and glossy.

*Pedicels*.—Moderate strength, average of 2.4 cm in length and 2 mm in width, held at about a 25° angle from vertical on sterile flowers and about a 10° angle from vertical on fertile flowers, 60A to 60B in color, surface is glabrous and glossy.

*Calyx*.—Fertile flowers; campanulate in form, average of 3 mm in length and 5 mm in diameter.

*Petals*.—Fertile flowers; average of 5, rotate in arrangement, ovate in shape, entire margin, acute apex, cuneate base, average of 4 mm in length and 2 mm in width, surface is glabrous and dull on both surfaces, color of upper surface (opening and mature flowers); 115D, color of lower surface (opening and mature flowers); 112D, not persistent, sterile flowers; 4, folded into center eye, about 3 mm in diameter, 144D in color, persistent.

*Sepals*.—Fertile flowers; average of 5, 60% fused towards base, rotate in arrangement, glabrous and slightly glossy surface (both surfaces), ovate in shape, entire margin, apex is short apiculate, cuneate base, an average of 3 mm in length and 2 mm in width, color when flower opens and mature on upper and lower surface; 144B with tips 144A, Sterile flowers; average of 4, unfused, rotate in arrangement, glabrous and dull surface (both surfaces), apex is short apiculate, reniform to broadly deltoid in shape, margin is entire to sparsely serrated, broadly apiculate apex, cuneate base, an average of 3 cm in length and 3.3 cm in width, color of upper surface when opening; 64C with base 145C to 145D flushed with 97B, color of lower surface when opening; 75A to 75B with base 145C.

Reproductive organs (fertile flowers):

*Stamens*.—Average of 10, anther is kidney-shaped, about 1 mm in length and 115D in color, filament is an average of 5 mm in length and 155C in color, pollen is moderate in quantity and 156D in color.

*Pistils*.—1, average of 2 mm in length, 3 stigmas are club-shaped, fused at base, and 145D in color, style is an average of 1 mm in length and 145B in color, ovary is inferior and 145A in color.

*Fruit and seed*.—Has not been observed under the conditions tested to date.

It is claimed:

1. A new and distinct cultivar of *Hydrangea* plant named 'Zulu' substantially as herein illustrated and described.

* * * * *